United States Patent [19]

Lee

[11] Patent Number: 5,376,676

[45] Date of Patent: Dec. 27, 1994

[54] PROCESS OF USING ANTI-INFLAMMATORY FURANONES AS SELECTIVE CALCIUM CHANNEL INHIBITORS

[75] Inventor: Gary C. M. Lee, Laguna Hills, Calif.

[73] Assignee: Allergan, Inc., Irvine, Calif.

[21] Appl. No.: 752,402

[22] Filed: Aug. 30, 1991

Related U.S. Application Data

[63] Continuation-in-part of Ser. No. 427,202, Oct. 25, 1989, Pat. No. 5,045,564, which is a continuation-in-part of Ser. No. 281,126, Dec. 7, 1988, abandoned.

[51] Int. Cl.$^5$ .............................................. A61K 31/34
[52] U.S. Cl. .................................... 514/473; 549/295
[58] Field of Search .......................................... 514/473

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |

FOREIGN PATENT DOCUMENTS

| | | |
|---|---|---|
| 133376 | 2/1985 | European Pat. Off. . |
| 209274 | 1/1987 | European Pat. Off. . |
| 295056 | 6/1987 | European Pat. Off. . |
| 350878 | 1/1990 | European Pat. Off. . |

OTHER PUBLICATIONS

Bonjuklian, et al., Chemical Abstracts, vol. 106, 156260c, p. 670 (1987).

Reynolds, et al, J. Am. Chem. Soc., 110, pp. 5172–5177 (1988).

Tocanne et al., Chemical Abstracts 69, 76581k, p. 7146 (1968).

Deems, et al, Biochimica et Biophysica Acta, 917 pp. 258–268 (1987).

Scheuer et al., Journal of the American Chemical Society 100:1 p. 307 (Jan. 4, 1978).

Graziano, et al., Chemical Abstracts 107, (1987), 236559t.

Roll et al., Org. Chem. 1988, 53 3276-8.

Negishi et al., J. Org. Chem. 45, pp. 5223–5225, (1980).

E. D. de Silva et al., "Tetrahedron Letters", 21:1611–1614 (1980).

Nakagawa et al., "Aldose reductase inhibitor from Palaun sponges" Chem. Abstract 106: 96126b (1986).

Tanaka, et al., The Chemical Society of Japan, Chemistry Letters, pp. 633–636 (1983).

Tanis, et al., Tetrahedron Letters, vol. 25, No. 40, pp. 4451–4454 (1984)-Furans in Synthesis 4. Silyl Furans as Butenolide Equivalents.

Graziano, et al, "Photosensitized Oxidation of Furans, Part 12, Solvent Effects In Thermal Rearrangement Of The 2,5-Peroxides Of 2,5-Unsubstituted Furans", J. Chem. Soc., Perkin Trans, 1, (8), 1833–9, Apr. 19, 1989.

David Nettleton, et al, Inflammation Research Association, Fifth International Conference Poster Session, Phospholipase A$_2$ Inhibition by Dihydrofuranones, Sep. 23–27, 1990.

Primary Examiner—C. Warren Ivy
Assistant Examiner—A. A. Owens
Attorney, Agent, or Firm—Gabor L. Szekeres; Robert J. Baran; Martin A. Voet

[57] ABSTRACT 4-($C_{10}$-$C_{20}$)alkyl-2(5H)-furanone compounds are selective calcium channel inhibitors and useful for treatment of diseases such as hypertension, angina, cardiac arrythmia, pulmonary hypertension, aortic insufficiency, Raynand's disease, migraine headaches, deficiency of platelet function, atherosclerosis, ischemia, reprofusion injury, bronchial asthma, esophageal spasm, dysmenorhea, allergic contact dermatitis, acute inflammatory response, glaucoma and as potentiators of chemotherapeutic agents in the treatment of tumors.

3 Claims, No Drawings

PROCESS OF USING ANTI-INFLAMMATORY FURANONES AS SELECTIVE CALCIUM CHANNEL INHIBITORS

CROSS-REFERENCE TO RELATED APPLICATION

The present application is a continuation-in-part of application Ser. No. 07/427,202 filed on Oct. 25, 1989, assigned to the same assignee as the present application, now expected to be issued as U.S. Pat. No. 5,045,564, which is itself a continuation-in-part of application Ser. No. 281,126, filed on Dec. 7, 1988, assigned to the same assignee as the present application, now abandoned.

BACKGROUND

Manoalide is a compound isolated from a marine sponge [E. D. de Silva et al., *Tetrahedron Letters* 21:1611–1614 (1980)] which has anti-inflammatory, immunosuppressive and analgesic properties. Manoalide the structure of which is shown below, includes a 5-hydroxy-2(5H)-furanone moiety, attached in the 4-position of the furanone ring to the rest of the molecule. Certain analogs of manolide, such as seco-manoalide and dehydroseco-manoalide also have anti-inflammatory activity. For further description of the biological activity of manoalide and some of its derivatives reference is made to U.S. Pat. Nos. 4,447,445, 4,786,651, 4,789,749 and to European Patent Application No. 0 133 376 (published on Feb. 20, 1985).

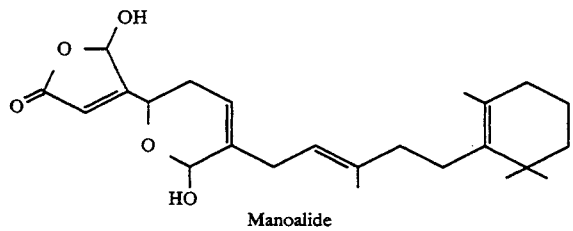

Manoalide

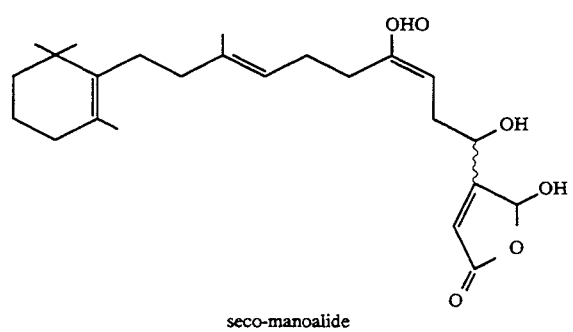

seco-manoalide

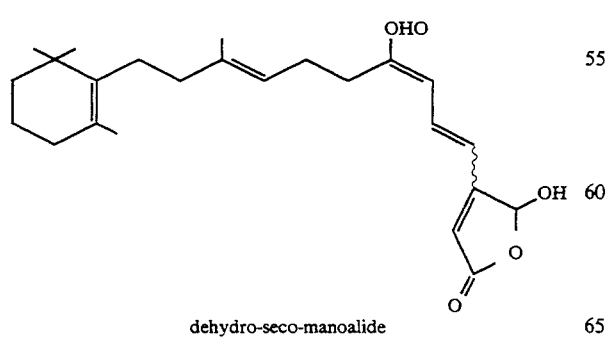

dehydro-seco-manoalide

Synthetic analogs of manoalide, particularly analogs having various substituents on the furanone moiety of manoalide, are described in patents and several applications for United States Letters Patent by the same inventor or co-inventor as in the present application, such as U.S. Pat. Nos. 4,935,530 (issued Jun. 19, 1990), 4,957,917 (issued Sep. 18, 1990), 5,013,850 (issued May 7, 1991), 5,037,811 (issued Aug. 6, 1991) and U.S. application Ser. Nos. 699,819 (filed May 13, 1991, pending), 426,243 (filed Oct. 25, 1991, pending), 427,268 (filed Oct. 25, 1989, allowed), 510,364 (filed Apr. 17, 1990, pending), 493,895 (filed Mar. 15, 1990, allowed), 510,367, (filed Apr. 17, 1990, allowed), 693,204 (filed Apr. 30, 1991, pending) and 693,201 (filed Apr. 30, 1991, pending).

Published European Patent Application No. 0 295 056 discloses 4-substituted 5-hydroxy-2(5H)-furanones having anti-inflammatory, immunosuppressive and antiproliferative activity where the substituents in the 4 position are a variety 1-hydroxy-alkyl, 1-acyloxy-alkyl and 1-carbamoyloxy-alkyl groups.

U.S. Pat. No. 4,855,320 discloses 5-arylalkyl-4-alkoxy-2(5H)-furanones as anti-convulsive and anti-epileptic agents.

Published European Patent Application No. 0 209 274 discloses 4-alkyl-5-hydroxy-2(5H)-furanones as anti-inflammatory and anti-allergy agents.

Chemical Abstracts Volume 107 236559t (1987) discloses 4-acyloxy 5-hydroxy-2(5H)-furanones.

U.S. Pat. No. 4,874,782 describes certain 4-substituted-5-hydroxy 2-(5H)-furanones as agents for treating inflammation, asthma or allergies.

U.S. Pat. No. 4,916,241 describes certain 4-substituted 5-hydroxy-2-(5H)-furanones as agents for modifying the balance between bone production and bone resorption in host animals.

An article by Tanaka et al. "DIANIONS OF —HYDROXY SULFONES: NEW AND GENERAL APPROACH TO SELECTIVE SYNTHESIS OF 2(5H)-FURANONES" Chemistry Letters pp 633–636, 1983 (The Chemical Society of Japan, discloses a synthetic route to 4-alkyl-2(5H)-furanones, including 4-octyl-2(5H)-furanone, and 4-decyl-2(5H)-furanone, without discussing any type of biological activity of these compounds.

An article by Tanis et al. "FURANS IN SYNTHESIS 4. SILYL FURANS AS BUTENOLIDE EQUIVALENTS" Tetrahedron Letters Volume 25, pp 4451–4454, 1984, also describes a synthetic route to 4-alkyl-2(5H)-furanones, including 4-decyl-2(5H)-furanone, without discussing any type of biological activity of these compounds.

THE INVENTION

The compounds of the present invention are represented by the following formula:

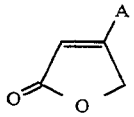

FORMULA I

Particular compounds of this invention are represented by Formula I in which:

A is —CH($R_1$)R;
R is $C_7$–$C_{20}$alkyl;
$R_1$ is hydroxy or $OCOR_2$;
$R_2$ is $C_1$–$C_{14}$alkyl or α-methylbenzylamino; or R is 2-(methoxy)ethoxymethoxymethyl and $R_1$ is OCO—($C_7$-$C_{14}$alkyl).

Specific compounds of this invention are, for example:

4-[1-dodecanoyloxy-2-(2-methoxyethoxy)methoxymethyl]-2(5H)-furanone, 4-(1-acetoxytridecyl)-2(5H)-furanone, 4-[—((R)-(+)-alpha-methylbenzylcarbamyloxy)-tridecyl]-2(5H)-furanone, and 4-(1-hydroxytridecyl)-2(5H)-furanone.

With respect to the compounds of Formula I where A is $C_8$-$C_{20}$ alkyl, preferably $C_{10}$-$C_{20}$ alkyl, it has been discovered that these compounds are selective calcium channel inhibitors, and therefore are useful as therapeutic agents for numerous conditions and diseases, detailed below. A particular example of such compound is 4-tridecyl-2(5H)-furanone.

Certain of the compounds of this invention contain chiral centers and accordingly, may be prepared as enantiomeric or diasteriomeric mixtures or in optically pure form. Unless otherwise specified herein, such preparations are racemates at each chiral center. However, the scope of the invention is not to be considered as limited to these forms but also to encompass the individual optical isomers of the compounds.

Compounds of the invention are prepared by procedures which are illustrated hereinbelow and described in more detail in the examples.

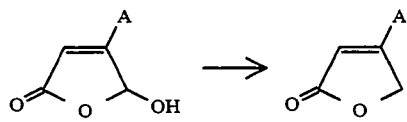

According to the above procedure, a 5-hydroxy-2(5H)-furanone is treated with a reducing agent, such as sodium borohydride, to give compounds of Formula I.

Alternatively, compounds of Formula I in which $R_1$ is $OCOR_2$ are prepared from compounds of Formula I in which $R_1$ is hydroxy by acylating with an acyl anhydride or halide.

The 5-hydroxy-2(5H)-furanone starting materials for the compounds of this invention are prepared by procedures which are illustrated hereinbelow and described in more detail in the examples.

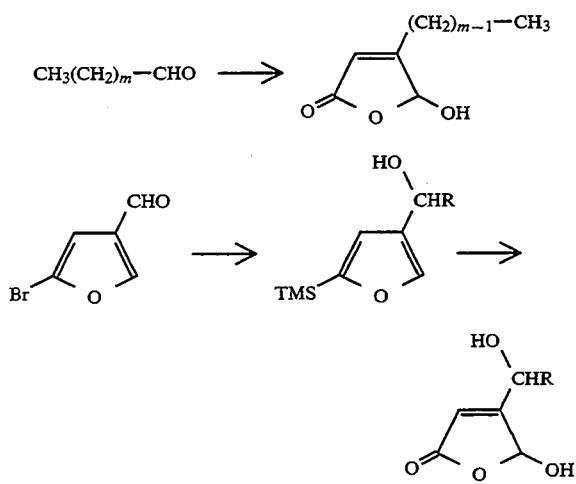

According to procedure I, an aldehyde is reacted with glyoxylic acid and phosphoric acid to give a 4-alkyl-5-hydroxy-2(5H)-furanone.

In procedure II, 5-bromo-3-furaldehyde is reacted with a Grignard reagent (RMgX) and the resulting mixture is treated with t-butyl lithium and trimethylsilyl chloride to give a 4-[R—CH(OH)]-2-trimethylsilylfuran. Also, the aldehyde group of 5-trimethylsilyl-3-furaldehyde may be reacted with 2-(methoxy)ethoxymethyl tributylstannylmethyl ether and the OH group O-alkanoylated. The 4-substituted-2-trimethylsilylfuran intermediates are oxidized using Rose Bengal as an initiator and irradiating to give the 4-substituted-5-hydroxy-2(5H)-furanones.

The intermediates for the compounds of Formula I in which A is CH(OCOC$_1$—C$_4$alkyl)—(C$_7$-C$_{20}$alkyl) are prepared by converting the aldehyde group of 5-trimethylsilyl-3- furaldehyde to a vinyl group, for example by Wittig reaction with an alkyl triphenylphosphonium bromide/butyl lithium, oxidizing the vinyl group using, for example, osmium tetroxide, then O-alkanoylating.

The 4-[R—CH(R$_1$)]-2-trimethylsilylfuran is converted to the corresponding 4-substituted 5-hydroxy-2(5H)-furanone by treating with oxygen and irradiating using an initiator such as Rose Bengal.

5-Trimethylsilyl-3-furaldehyde may be prepared by brominating 3-furaldehyde to give 5-bromo-3-furaldehyde which is converted to the dimethylacetal, then treated with t-butyl lithium and trimethylsilyl chloride.

A preferred method for preparing 5-trimethylsilyl-3-furaldehyde is by reacting lithium morpholide with 5-bromo-3-furaldehyde to protect the aldehyde group, then reacting with t-butyl lithium and trimethylsilyl chloride to give 5-trimethylsilyl-3-furaldehyde.

An improved method for preparing 5-trimethylsilyl-3- furaldehyde consists of reacting lithium morpholide with 3-furaldehyde, followed by secondary-butyl lithium, followed by trimethylsilyl chloride. This method is also advantageous for the preparation of 5-triethylsilyl-3-furaldehyde using triethylsilyl chloride. 5-Triethylsilyl-3-furaldehyde is useful as an intermediate in place of the trimethyl compound in methods described herein for preparing compounds of this invention.

In addition, this invention relates to pharmaceutical compositions containing the compounds of Formula I as active ingredients and to methods of using the compounds and pharmaceutical compositions of this invention to produce anti-inflammatory, immunosuppressant and anti-proliferative activity. These compounds are useful in treating inflammation, in suppressing unwanted immune responses and in retarding proliferation of cells. Uses include treatment of rheumatoid arthritis, osteoarthritis, rheumatic carditis and autoimmune diseases such as allergic diseases, bronchial asthma and myasthenia gravis and ocular and dermal inflammatory diseases. The compounds are useful in treating psoriasis, acne, atopic diseases and allergic conjunctivitis. They are also useful as adjuvant therapy associated with organ and tissue transplants.

The activity of the compounds of this invention is demonstrated by the effect on calcium homeostasis. The compounds are calcium channel antagonists. This activity is shown by effect on intracellular calcium levels in experiments using gastric glands, spleen cells, epithelial cells, $GH_3$ cells, etc. Calcium is inhibited from entering through the plasma membrane calcium channels and calcium release from intracellular stores is also blocked.

Modification of calcium homeostasis (calcium channel inhibition) and particularly the selctive inhibition of calcium channel is expected to have application in the following mammalian, including human, conditions and diseases. In the cardiovascular field: hypertension, angina, cardiac arrythmia, pulmonary hypertension, aortic insufficiency, Raynand's disease, migraine headaches, deficiency of platelet function, and atherosclerosis. In the CNS field: ischemia, reprofusion injury (calcium channel inhibitor inhibits release of neurotoxin transmitters). In the pulmonary field: bronchial asthma.

In the spasmolytic field: esophageal spasm, dysmenorhea. In the inflammatory and allergy field: allergic contact dermatitis, acute inflammatory response. In the oncological field calcium channel inhibitors are expected to potentiate chemotherapeutic agents. Calcium channel inhibitors are also expected to be useful for the treatment of glaucoma.

The compounds are also useful as agents for modifying the balance between bone production and bone resorption in a host animal, including man.

The compounds of this invention differ from manoalide in that they demonstrate weak or no activity as inhibitors of the enzyme phospholipase $A_2$ in vitro or of phosphoinositide-specific phospholipase C.

The selective calcium channel activity of 4-alkyl-2(5H)-furanones (especially as compared to the corresponding 4-alkyl-2(5H)-5-hydroxy furanones) which has been discovered in accordance with the present invention is illustrated in Table 1 where results of calcium channel (mobilization) inhibition assay, (TRH and KCl induced) inhibition of phospholipase $A_2$ assay ($PLA_2$), and inhibition of phosphoinositide specific phospholipase C assay (PLC), are described with respect to the following compounds:

4-tridecyl-2(5H)-furanone (Compound 1);
4-tridecyl-5-hydroxy-2(5H)-furanone (Compound 2);
manoalide.

TABLE 1

| Compound # | $IC_{50}$ | | $Ca^{2+}$ | |
|---|---|---|---|---|
| | $PLA_2$ | PLC | TRH | KCl |
| 1 | >3.3 | >100 | 2.6 | 1.5 |
| 2 | 0.09 | >100 | 3 | 3 |
| manoalide | 0.03 | 3 | 0.6 | 0.8 |

For the interpretation of data shown in Table 1 it is noted that a compound is considered active inhibitor of the phospholipase enzymes ($PLA_2$ and PLC) if the $IC_{50}$ concentration is less than 10 micromolar, preferably less than 1.0 micromolar. Also, a compound is considered an active inhibitor of $Ca^{2+}$ channel mobilization if the $IC_{50}$ in the TRH and KCl induced assays is less than 10 micromolar, preferably close to or less than 1 micromolar. Selectivity between calcium channel inhibition and phospholipase inhibition, as well as selectivity between inhibition of the two calcium channels are both desirable properties. It can be seen that 4-tridecyl-2(5H)-furanone (Compound 1) is a selective calcium channel inhibitor.

The compounds are active in reducing inflammation in the mouse ear anti-inflammatory assay in vivo.

The compounds of this invention, like manoalide, appear to be devoid of the endocrine properties of the glucocorticoids while having anti-inflammatory and immunosuppressive properties.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula I and pharmaceutical carriers suitable for the route of administration. Standard methods for formulating pharmaceutical compositions of this type may be found in Remington's Pharmaceutical Sciences, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
|---|---|
| Water/glycol mixture (15% or more glycol) | 50–99 |
| Fatty alcohol | 1–20 |
| Non-ionic surfactant | 0–10 |
| Mineral oil | 0–10 |
| Typical pharmaceutical adjuvants | 0–5 |
| Active ingredient | 0.05–5 |

A typical ointment formulation may contain the following:

| Ingredients | Parts by Weight |
|---|---|
| White petrolatum | 40–94 |
| Mineral oil | 5–20 |
| Glycol solvent | 1–15 |
| Surfactant | 0–10 |
| Stabilizer | 0–10 |
| Active ingredient | 0.05–5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
|---|---|
| Lactose, spray-dried | 40–99 |
| Magnesium stearate | 1–2 |
| Cornstarch | 10–20 |
| Active ingredient | 0.001–20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The following examples are intended to illustrate the invention but are not limiting. All temperatures are in degrees Centigrade. NMR data are recorded in delta ppm.

EXAMPLE 1

5-Trimethylsilyl-3-furaldehyde n-Butyl lithium (a 1.6M solution in hexane; 31.0 ml, 49.7 mmol) was added dropwise to a solution of morpholine (4.33 ml, 49.7 mmol; freshly distilled from barium oxide) in tetrahydrofuran at −78° under argon. After 15 minutes, a solution of 5-bromo-3-furaldehyde (7.5 g, 49.7 mmol) in tetrahydrofuran (THF) was added dropwise. Stirring was continued for 30 min. and n-butyl lithium (a 1.6M solution in hexane; 46.6 ml, 74.5 mmol) was added dropwise. After 1 hour at −78°, chlorotrimethylsilane (18.9 ml, 149 mmol) was added and stirring continued while the cooling bath attained room temperature. The reaction mixture was quenched with 10% hydrochloric acid and the phases were separated. The aqueous phase was stirred, in the presence of ethyl ether (30 ml), with 10% hydrochloric acid at 0° C. for ½ hour. The organic phases were combined, washed (brine), dried (magnesium sulfate) and evaporated down. The residue was distilled under vacuum to give the title aldehyde as a colorless oil b.p. 48–50°/0.25 torr.

$^1$H NMR (CDCl$_3$): 0.29 (5.9H), 6.98 (5.1H), 8.25 (5.14) and 9.95 (5.1H)

$^{13}$C NMR (CDCl$_3$): −2.0, 116.2, 128.9, 155.3, 164.1 and 184.5.

MS m/e: Exact mass calculated for C$_8$H$_{12}$O$_2$S: 168.0607, found 168.0588.

EXAMPLE 2

Alternative Preparation of 5-trimethylsilyl-3-furaldehyde n-Butyl lithium (a 2.5M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at −78° for 7 hours before trimethylsilyl chloride (27 ml, 2.6 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with ethyl ether. All the organic phases were combined, dried (magnesium sulfate) and evaporated down to give a light brown oil, which was purified by flash chromatography on silica using 2% ethyl ether/hexane. Fractions with R$_f$ of about 0.30 (silica, 10% ethyl ether/hexane) on evaporation gave the title aldehyde as a light yellow oil, b.p. 48°–50°/0.25 torr.

$^1$H NMR (CDCl$_3$): 0.29 (s, 9H), 6.98 (s, 1H), 8.25 (s, 1H) and 9.95 (s, 1H).

$^{13}$C NMR (CDCl$_3$): −2.0, 116.2, 128.9, 155.3, 164.1 and 184.5.

EXAMPLE 3

4-(1-Hydroxytridecyl)-2-trimethylsilylfuran

A solution of 5-trimethylsilyl-3-furaldehyde (0.5 g, 2.97 mmol) in tetrahydrofuran (5 ml) was added to a solution of dodecyl magnesium bromide (5.95 mmol; prepared from 1.48 g dodecyl bromide and 146 mg magnesium turnings in 30 ml tetrahydrofuran) at room temperature. After 2 hours, the mixture was quenched with ammonium chloride solution and extracted thoroughly with ethyl ether. Evaporation of the dried (magnesium sulfate) extracts gave an oil which was flash chromatographed on silica using 10% ethyl ether/hexane. Fractions with R$_f$ about 0.13 on evaporation gave the title alcohol as a pale yellow oil.

$^1$H NMR (CDCl$_3$): 0.26 (s, 9H), 0.89 (t, 3H, J=7.3 Hz), 1.27 (broad s, 16H), 1.62 (br, 1H), 1.75 (m, 2H), 4.65 (t, 1H, J=6.8 Hz), 6.63 (s, 1H) and 7.57 (s, 1H).

MS m/e (% abundance): 293 (M+ —OH, 2), 221 (5), 177 (31), 175 (33), 97 (14), 87 (10), 85 (64), 83 (100), 73 (14) and 57 (12).

4-(1-Hydroxytridecyl)-5-hydroxy-2(5H)-furanone

A mixture of 4-(1-hydroxytridecyl)-2-trimethylsilylfuran (271.2 mg, 0.8 mmol) and Rose Bengal (5 mg) in tetrahydrofuran (10 ml) was exposed to singlet oxygen for 2 hours at −78°. The residue, after solvent removal, was flash chromatographed on silica using 70% ethyl ether/petroleum ether. Fractions with R$_f$ of about 0.09 (60% ethyl ether/petroleum ether) on evaporation afforded the captioned furanone as a colorless oil.

$^1$H NMR (CDCl$_3$): 0.91 (t, 3H, J=6.8 Hz), 1.29–1.34 (broad m, 20H), 1.75 (m, 2H), 4.00 (br, 2H, exchanged with D$_2$O), 4.68 (m, 1H), 5.99 (s, 1H), 6.10 (d, 1H, J=7.5 Hz, sharpened into a singlet on D$_2$O exchange), 6.15 (d, 1H, sharpened into a singlet on D$_2$O exchange) and 6.28 (s, 1H).

$^{13}$C NMR (CDCl$_3$): 14.1, 22.7, 25.1, 25.1, 25.7, 29.1, 29.3, 29.5, 29.6, 29.6, 29.8, 31.9, 35.3, 35.6, 68.0, 68.2, 97.5, 97.6, 117.6, 118.1, 168.9, 170.4, 170.6 and 170.9.

MS m/e: exact mass calculated for C$_{17}$H$_{31}$O$_4$ (M+H)+ 299.2222, found 299.2231.

4-(1-Hydroxytridecyl)-2(5H)-furanone

Sodium borohydride (68.0 mg, 1.8 mmol) was added to a solution of 4-(1-hydroxytridecyl)-5-hydroxy-2(5H)-furanone (268 mg, 0.9 mmol) in tetrahydrofuran (5 ml) and methanol (5 drops) at room temperature. After 5 hours, the mixture was quenched with dilute hydrochloric acid and extracted with ethyl acetate (discarded). The aqueous phase was evaporated to near dryness, saturated with sodium chloride and extracted thoroughly with ethyl acetate. Evaporation of the dried (magnesium sulphate) extracts gave an oil, which was purified by preparation TLC (silica plate; developed with 60% ethyl ether/hexane). The title furanone was obtained as an off-white solid.

$^1$H NMR (CDCl$_3$): 0.91 (t, 3H, J=6.4 Hz), 1.28 (brs, 20H), 1.70 (m, 2H), 4.66 (t, 1H, J=7.5 Hz), 4.90 (brs, 2H) and 5.98 (brs, 1H).

$^{13}$C NMR (mixtures of diasteriomers) (CDCl$_3$): 14.0, 22.6, 25.0, 25.2, 25.4, 29.2, 29.4, 29.5, 31.4, 31.8, 35.1, 35.4, 36.2, 40.8, 62.5, 68.4, 70.1, 71.2, 71.4, 72.2, 83.2, 114.3, 173.9 and 174.4.

MS m/e: exact mass calculated for C$_{17}$H$_{30}$O$_3$ (M+) 282.2194, found 282.2187.

EXAMPLE 4

4-(1-Acetoxytridecyl)-2(5H)-furanone

A mixture of 4-(1-hydroxytridecyl)-2(5H)-furanone (62 mg, 0.22 mmol), acetic anhydride (½ ml), pyridine (½ ml) and tetrahydrofuran (2 ml) was stirred at room temperature for 14 hours. After most of the solvent was removed under high vacuum, the residue was purified by preparative TLC (silica plate; 60% ethyl ether/hexane). The title furanone was obtained as a pale yellow oil.

$^1$H NMR (CDCl$_3$): 0.89 (t, 3H, J=6.3 Hz), 1.26 (brs, 20H), 1.80 (m, 2H), 2.09 (s, 3H), 2.14 (s, 3H), 4.82 (dd, 2H, J=15.0 Hz), 5.65 (t, 1H, J=7.5 Hz) and 5.98 (brs, 1H).

$^{13}$C NMR (CDCl$_3$): 14.0, 20.7, 20.8, 22.5, 22.6, 24.8, 24.9, 25.1, 25.3, 29.1, 29.3, 29.4, 29.6, 31.0, 31.7, 31.8, 32.2, 33.5, 35.0, 38.7, 39.7, 64.1, 69.2, 69.7, 70.8, 73.8, 82.6, 116.2, 167.7, 169.9 and 172.8.

MS m/e: Exact mass calculated for C$_{19}$H$_{32}$O$_4$ (M+) 324.2300, found 324.2296.

EXAMPLE 5

5-Bromo-3-furaldehyde

3-Furaldehyde (11.6 g, 121 mmol) was added dropwise to a solution of anhydrous aluminum bromide (48.1 g, 180 mmol) in dry dibromomethane (200 ml). An exothermic reaction ensued and a dark brown color developed. After 10 minutes, bromine (6.82 ml, 133 mmol) was added dropwise and the mixture was warmed at approximately 50° for 1 hour. On cooling, the mixture was poured into crushed ice and the organic layer was separated. The aqueous phase was extracted with methylene chloride. All the organic layers were combined, washed (successively with water, 5% aqueous sodium bicarbonate and brine) and filtered through celite. Distillation of the dried (magnesium sulfate) extract gave 5-bromo-3-furaldehyde as a colorless oil: bp 55°/0.25 torr.

$^1$H NMR (CDCl$_3$): 6.80 (s, 1H), 8.10 (s, 1H) and 9.91 (s, 1H).

4-(1-Hydroxynonyl)-2-trimethylsilylfuran

A mixture of 1-bromooctane (1.33 g, 6.9 mmol) and magnesium turnings (174 mg, 7.3 mmol) in tetrahydrofuran (8 ml) was refluxed under argon for 60 minutes. After cooling to 0°, a solution of 5-bromo-3-furaldehyde (1.21 g, 6.9 mmol) in THF (1 ml) was added and conditions maintained for 60 min. The mixture was further cooled to −78° and tert-butyl lithium (a 1.7M solution in pentane, 4.26 ml, 7.3 mmol) was added dropwise, followed by chlorotrimethylsilane (2.63 ml, 20.7 mmol) after 1 hour. Stirring was continued overnight while the cooling bath attained room temperature. The mixture was quenched with saturated aqueous ammonium chloride, diluted with water (15 ml) and extracted with ether. Evaporation of the dried (magnesium sulfate) extract gave a brown oil, which was subjected to flash chromatography on silica using 15% ethyl ether/petroleum ether. Fractions with R$_f$ of about 0.2 on evaporation gave the captioned compound as a yellow oil.

$^1$H NMR (CDCl$_3$): 0.32 (s, 9H), 0.94 (t, 3H, J=7.3 Hz), 1.33 (broad s, 12H), 1.70 (br, 1H), 1.85 (m, 2H), 4.71 (t, 1H, J=6.8 Hz), 7.32 (s, 1H) and 7.63 (s, 1H).

$^{13}$C NMR (CDCl$_3$): −1.70, 14.0, 22.6, 25.4, 25.6, 25.7, 29.2, 29.5, 31.8, 36.8, 37.6, 37.9, 66.7, 66.9, 110.2, 118.3, 129.2, 140.4, 143.4 and 161.2.

MS m/e (% abundance): 282 (M+, 2) 265 (3), 249 (4), 247 (4), 182 (3), 177 (11), 175 (12), 169 (9), 167 (3) and 147 (5); exact mass calculated for C$_{16}$H$_{30}$SiO$_2$ 282.2015, found 282.2009.

4-(1-Acetoxynonyl)-2-trimethylsilylfuran

A mixture of 4-(1-hydroxynonyl)-2-trimethylsilylfuran (1.65 g, 5.9 mmol), acetic anhydride (2 ml) and pyridine (3 ml) was stirred under argon at approximately 20° for 17 hours. After most of the solvent was removed under high vacuum (less than 40° C.), the residue was dissolved in ether (40 ml) and washed thoroughly with aqueous copper sulfate and water. Drying (magnesium sulfate) and evaporation gave a brown oil, which was flash chromatographed on silica using 5% ethyl ether/petroleum ether. Fractions with R$_f$ 0.32 on evaporation afforded 4-(1-acetoxynonyl)-2-trimethylsilylfuran as a pale yellow oil.

$^1$H NMR (CDCl$_3$): 0.26 (s, 9H), 0.89 (t, 3H, J=7.6 Hz), 1.27 (broad s, 12H), 1.90 (m, 2H), 2.06 (s, 3H), 5.78 (t, 1H, J=6.7 Hz), 6.60 (s, 1H) and 7:61 (s, 1H).

$^{13}$C NMR (CDCl$_3$): −1.73, 14.0, 21.1, 21.2, 22.6, 25.3, 25.5, 29.2, 29.2, 29.4, 31.8, 34.4, 34.8, 68.0, 68.3, 68.6, 110.5, 118.6, 125.0, 141.8, 144.4, 161.1 and 170.4.

MS m/e (% abundance): 325 (M+ +1, 5), 324 (21), 283 (13), 282 (56), 265 (16), 183 (27), 170 (36), 169 (41), 154 (14), 153 (13), 117 (32) and 73 (100); Exact mass calculated for C$_{18}$H$_{32}$SiO$_3$ 324.2121, found 324.2115.

4-(1-Acetoxynonyl)-5-hydroxy-2(5H)-furanone

A mixture of 4-(1-acetoxynonyl)-2-trimethylsilylfuran (323 mg, 0,9 mmol) and Rose Bengal (5 mg) in THF (10 ml) was exposed to singlet oxygen for 5.5 hours at −78°. The residue, after solvent removal, was flash chromato- graphed on silica using 60% ethyl ether/petroleum ether. Fractions with R$_f$ 0.13 on evaporation afforded the captioned compound as a colorless solid, mp 54°–5°.

$^1$H NMR (CDCl$_3$): 0.96 (t, 3H, J=6.7 Hz), 1.34 (broad s, 12H), 1.89 (m, 2H), 2.20 (s, 3H), 2.21 (s, 3H), 4.54 (d, 1H, J=7.6 Hz, exchanged with D$_2$O), 5.12 (d, 1H, J=10.5 Hz, exchanged with D$_2$O), 5.47 (t, 1H, J=6.3 Hz), 5.55 (t, 1H, J=6.3 Hz), 6.06 (2d+s) and 6.26 (d, 1H, J=7.3 Hz).

$^{13}$C NMR (CDCl$_3$): 14.0, 20.8, 22.6, 24.9, 25.0, 29.1, 29i3, 31.7, 32.9, 33.0, 69.3, 69.8, 98.0, 98.2, 118.3, 119.0, 166.7, 167.1, 170.0 and 171.1.

MS m/e: exact mass calculated for C$_{15}$H$_{24}$O$_5$ 284.1624, found 284.1691.

4-(1-Acetoxynonyl)-2(5H)-furanone

Sodium borohydride (12.9 mg, 0.34 mmol) was added to a solution of 4-(1-acetoxynonyl)-5-hydroxy-2(5H)-furanone (48.1 mg, 0.17 mmol) in tetrahydrofuran (5 ml) and methanol (0.5 ml) at room temperature. After 40 minutes, most of the solvent was removed and water (5 ml) was added. Extraction (dichloromethane) and evaporation of the dried (magnesium sulphate) extracts gave a residue, which was flash chromatographed on silica using 60% ethyl ether/petroleum ether. Fractions with R$_f$ of about 0.40 on evaporation afforded the title furanone as a colorless oil.

$^1$H NMR (CDCl$_3$): 0.95 (brt, 3H), 1.33 (brs, 12H), 1.83 (m, 2H), 2.19 (s, 3H), 4.83 (d, 1H, J=15.0 Hz), 4.91 (d, 1H, J=15.0 Hz), 5.69 (brt, 1H) and 6.03 (s, 1H).

$^{13}$C NMR (CDCl$_3$): 14.0, 20.7, 22.6, 24.8, 29.1, 29.3, 31.7, 33.5, 69.8, 70.8, 116.3, 167.7, 170.0 and 172.8.

MS m/e: exact mass calculated for $C_{15}H_{24}O_4$ (M+) 268.1675, found 268.1678.

EXAMPLE 6

4-[1-((R)-(+)-α-Methylbenzylcarbamyloxy)tridecyl]-2(5H)-furanone

A solution of (R)-(+)-α-methylbenzyl isocyanate (31 mg, 0.21 mmol) in tetrahydrofuran (1 ml) was added to a solution of 4-(1-hydroxytridecyl)-2(5H)-furanone (20 mg, 0.07 mmol) and triethylamine (30 μl, 0.21 mmol) in tetrahydrofuran (1 ml) at room temperature. Stirring was continued for 2 days and the mixture was quenched with water. Extraction (dichloromethane) and evaporation of the dried (magnesium sulphate) extracts gave an oil, which was purified by preparative TLC (silica plate; developed with 60% ethyl ether/hexane). The title furanone was isolated as low melting colorless plates.

$^1$H NMR (mixture of diasteriomers) (CDCl$_3$): 0.94 (t, 3H, J=7.1 Hz), 1.31 (brs, 20H), 1.45 (d, 3H, J=6.9 Hz), 1.70 (m, 2H), 4.40 (m, 1H), 4.70 (m, 2H), 4.91 (brs, 2H), 6.00 (brs, 1H) and 7.25 (m, 5H).

$^{13}$C NMR (mixture of diasteriomers) (CDCl$_3$): 14.1, 22.7, 23.4, 25.0, 25.5, 29.3, 29.5, 29.6, 31.3, 31.9, 35.7, 36.5, 41.0, 50.3, 68.8, 70.0, 71.0, 72.6, 76.4, 114.9, 125.7, 125.9, 127.2, 127.4, 128.6, 128.7, 144.0 and 172.4.

MS m/e (% abundance): 283(M+—$C_9H_{10}NO$, 43), 237(70), 131(100) and 91(72).

EXAMPLE 7

2-Methoxyethoxymethyl Tributylstannylmethyl Ether

Tributyltin hydride (2.69 ml, 0.01 mol) was added dropwise to a solution of lithium diisopropylamide (a 1.5M solution in cyclohexane; 6.7 ml, 0.01 mol) in tetrahydrofuran (20 ml) at 0° under argon. After 15 minutes, paraformaldehyde (300 mg, 0.01 mol) was added, followed by 2-methoxyethoxymethyl chloride (1.15 ml, 0.01 mol) after 3 hours. Stirring was continued at room temperature for 12 hours and the mixture was quenched with water. Extraction (ethyl ether) and evaporation of the dried (magnesium sulphate) extracts gave an oil, which was flash chromatographed on silica using 5% ethyl ether/petroleum ether. Fractions with R$_f$ of about 0.24 on evaporation afforded the desired ether as a colorless oil (1.11 g, 27%).

$^1$H NMR (CDCl$_3$) 0.92 (m, 15H), 1.35 (m, 6H), 1.55 (m, 6H), 3.44 (s, 3H), 3.60 (m, 2H), 3.70 (m, 2H), 3.80 (dd, 2H), and 4.65 (s, 2H).

$^{13}$C NMR (CDCl$_3$) 8.7, 13.5, 27.1, 28.8, 57.5, 58.8, 66.3, 71.7 and 98.4.

MS m/e (% abundance) 428 ((M+NH$_4$)+, 8), 353 (100) and 296(81).

4-[1-Dodecanoyloxy-2-(2-methoxyethoxy)methoxyethyl]-2-trimethylsilylfuran n-Butyl lithium (a 1.6M solution in hexane; 0.74 ml, 1.18 mmol) was added to a solution of 2-methoxyethoxy-methyl tributylstannylmethyl ether (481.6 mg, 1.18 mmol) in tetrahydrofuran (5 ml) at −78° under argon. After 10 minutes, a solution of 5-trimethylsilyl-3-furaldehyde (198 mg, 1.18 mmol) was added, followed by lauroyl chloride (0.26 ml, 1.18 mmol) after 20 minutes. Stirring was continued at room temperature for 48 hours and the mixture was quenched with water. Extraction (ether) and evaporation of the dried (magnesium sulphate) extracts gave an oil, which was flash chromatographed on silica using 20% ethyl ether/petroleum ether. Fractions with R$_f$ of about 0.27 (30% ethyl ether/petroleum ether) on evaporation afforded the title ester as a pale yellow oil.

$^1$H NMR (CDCl$_3$): 0.26 (s, 9H), 0.89 (t, 3H, J=6.9 Hz), 1.27 (brs, 16H), 1.65 (m, 2H), 2.34 (t, 2H, J=7.7 Hz), 3.41 (s, 3H), 3.58 (m, 2H), 3.67 (m, 2H), 3.84 (m, 2H), 4.77 (s, 2H), 6.05 (dd, 1H, J=7.5 Hz, 3.8 Hz), 6.62 (s, 1H) and 7.66 (s, 1H).

MS m/e (% abundance): 488 ((M+NH$_4$)+, 26), 271 (100), 195 (42), 123 (25) and 90 (18).

4-[1-Dodecanoyloxy-2-(2-methoxyethoxy)methoxyethyl]-5-hydroxy-2(5H)-furanone

A mixture of 4-[1-dodecanoyloxy-2-(2-methoxyethoxy)methoxyethyl]-2-trimethylsilylfuran (229 mg, 0.49 mmol) and Rose Bengal (5 mg) in tetrahydrofuran (7 ml) was exposed to singlet oxygen for 2 hours at −78°. The residue, after solvent removal, was purified by preparative TLC (silica plate; developed with ethyl ether/petroleum ether). The title ester was obtained as a colorless oil.

$^1$H NMR (CDCl$_3$): 0.89 (t, 3H, J=6.9 Hz), 1.27 (brs, 16H), 1.65 (brt, 2H), 2.43 (t, 2H, J=7.8 Hz), 3.40 (s, 3H), 3.05 (m, 2H), 3.30 (m, 2H), 3.95 (m, 2H), 4.74 (s, 2H), 5.70 (brm, 1H), 6.11 (s, 1H) and 6.14 (s, 1H).

$^{13}$C NMR (CDCl$_3$): 14.1, 22.7, 24.8, 29.1, 29.2, 29.3, 29.4, 29.6, 31.9, 34.0, 58.9, 67.2, 67.4, 68.5, 71.7, 95.6, 97.9, 98.1, 120.2, 169.6 and 172.9.

MS m/e: exact mass calculated for $C_{22}H_{42}NO_8$(M+NH$_4$)+ 448.2910, found 448.2890.

4-[1-Dodecanoyloxy-2-(2-methoxyethoxy)methoxyethyl]-2(5H)-furanone

A mixture of 4-[1-dodecanoyloxy-2-(2-methoxyethoxy)methoxyethyl]-5-hydroxy-2(5H)-furanone (31.8 mg, 73.9 mmol) and sodium borohydride (5.6 mg, 0.15 mmol) in tetrahydrofuran (2 ml) containing methanol (5 drops) was stirred at room temperature for 1 hour. The mixture was quenched with water and extracted with dichloromethane. The residue, after solvent removal, was purified by preparative TLC (silica plate; developed with 60% ethyl ether/petroleum ether). The title furanone was obtained as a colorless oil.

$^1$H NMR (CDCl$_3$): 0.92 ( t, 3H, J=6.0 Hz), 1.30 (brs, 16H), 1.75 (brm, 2H), 2.41 (t, 2H, J=7.6 Hz), 3.43 (s, 3H), 3.60 (m, 2H), 3.70–3.90 (m, 4H), 4.45 (brm, 2H), 4.77 (brs, 2H), 5.50 (brt, 1H) and 6.05 (br, 1H).

$^{13}$C NMR (CDCl$_3$): 14.1, 22.7, 24.8, 29.0, 29.2, 29.3, 29.4, 29.6, 31.9, 34.0, 34.3, 58.5, 58.9, 59.0, 66.9, 67.4, 67,7, 68.5, 71.4, 71.6, 95.5, 95.6, 117.2, 165.4 and 172.5.

MS m/e (% abundance): 432 ((M+NH$_4$)+, 43), 415 (M++1, 10), 326 (9), 232 (38), 215 (100), 128 (41), 123 (12), 106 (16), 94 (36) and 89 (29).

EXAMPLE 8

5-Hydroxy-4-octyl-2(5H)-furanone

A mixture of decyl aldehyde (10 g, 64 mmol), glyoxylic acid monohydrate (5.6 g, 61 mmol) and 85% phosphoric acid (10 ml) was warmed at approximately 80° for 24 hours. On cooling, the solution was diluted with ethyl ether/dichloromethane (1:1, 50 ml each) and washed thoroughly with brine (5 times). The organic layer was dried (magnesium sulfate), evaporated down and purified by flash chromatography on silica using 40% ethyl acetate/hexane as eluant. Fractions with R$_f$ of about 0.14 on evaporation afforded the title furanone contaminated with the ring-opened form. The mixture was used directly in the next stage.

4-Octyl-2(5H)-furanone

Sodium borohydride (318 mg, 8.4 mmol) was added to 5-hydroxy-4-octyl-2(5H)-furanone (590 mg, 2.8 mmol) in tetrahydrofuran (5 ml) and methanol (1 ml) at room temperature. After 2 hours stirring, most of the solvent was removed and water (10 ml) was added. Extraction (dichloromethane) and evaporation of the dried (magnesium sulphate) extracts gave a residue, which was purified by preparative TLC (silica plate, developed with 60% ethyl ether/petroleum ether). The title furanone was obtained as a colorless solid: mp 65°–66°.

$^1$H NMR (CDCl$_3$): 0.86 (brt, 3H), 1.25 (brs, 10H), 1.45 (m, 2H), 2.51 (m, 2H), 4.21 (brs, 2H) and 5.98 (s, 1H).

$^{13}$C NMR (CDCl$_3$): 14.1, 22.7, 28.9, 29.2, 29.3, 29.7, 29.9, 31.9, 65.8, 112.5, 164.8 and 170.6.

MS m/e: Exact mass calculated for C$_{12}$H$_{20}$O$_2$ (M$^+$) 196.1463, found 196.1468.

EXAMPLE 9

Triethylamine (0.55 ml, 3.95 mmol), followed by oxalyl chloride (0.34 ml, 3.95 mmol) was added dropwise to a solution of 3-(1-hydroxytridecyl)-5-trimethylsilylfuran (890 mg, 2.63 mmol) in anhydrous dichloromethane (10 ml) at 0°. After 40 minutes, the reaction was quenched with ice water. Extraction (dichloromethane) and evaporation of the dried (magnesium sulfate) extracts gave an oil, which was purified by flash chromatography on silica using 5% ethyl ether/hexane. Fractions with R$_f$ of about 0.37 on evaporation gave 3-(1-chlorotridecyl)-2-trimethylsilylfuran as a pale yellow oil, solidified to a colorless solid on storage at −20°.

$^1$H NMR (CDCl$_3$): 0.26 (s, 9H), 0.89 (t, 3H, J=6.3 Hz), 1.26 (brs, 20H), 1.85–2.05 (2m, 2H), 5.87 (t, 1H, J=7.5 Hz), 6.63 (d, 1H, J=2.3 Hz) and 7.66 (d, 1H, J=2.4 Hz).

MS m/e (% abundance): 321 (M$^+$—Cl, 57), 180 (14), 154 (43), 153 (16), 75 (13) and 73 (100).

A mixture of this intermediate and Rose Bengal in tetrahydrofuran is exposed to singlet oxygen at −78° for 2 hours. The solvent Is removed and the residue purified (TLC) to give 4-(1-chlorotridecyl)-5-hydroxy-2(5H)-furanone.

Treating the above prepared 5-hydroxyfuranone in tetrahydrofuran and methanol, with sodium borohydride by the procedure of Example 5 gives 4-(1-chlorotridecyl)-2(5H)-furanone.

EXAMPLE 10

(E),(Z)-3-(2-Tridecenyl)-5-trimethylsilylfuran n-Butyl lithium (a 1.6M solution in hexane: 5.58 ml, 8.9 mmol) was added dropwise to a solution of dodecyltriphenylphosphonium bromide (4.57 g, 8.9 mmol) in tetrahydrofuran (35 ml) at 0° under argon. After 25 min., a solution of 5-trimethylsilyl-3-furaldehyde (1 g, 5.9 mmol) in tetrahydrofuran (3 ml) was added. Stirring was continued for 1 hour at 0° and the mixture was quenched with methanol/water (1:1, 60 ml). Extraction (hexane/ether, 1:1), washing (brine) and evaporation of the dried (magnesium sulphate) extracts gave an oil, which was purified by flash chromatography (silica) using 5% ethyl ether/hexane. Fractions with R$_f$ of about 0.8 on evaporation afforded the title olefin as a pale yellow oil.

$^1$H NMR (CDCl$_3$) (E)-isomer: 0.31 (s, 9H), 0.92 (t, 3H, J=7.1 Hz), 1.30 (brs, 18H), 2.29 (q, 2H, J=7.3 Hz), 5.95, 6.00 (dt, 1H, J=15.0 Hz, 7.5 Hz), 6.25 (d, 1H, J=15 Hz), 6.68 (s, 1H) and 7.66 (s, 1H).

(Z)-isomer: 0.30 (s, 9H), 0.92 (t, 3H, J=7.1 Hz), 1.30 (brs, 18H), 2.15 (q, 2H, J=7.3 Hz), 5.55, 5.60 (dt, 1H, J=11.5 Hz, 5.5 Hz), 6.15 (d, 1H, J=11.5 Hz), 6.77 (s, 1H) and 7.58 (s, 1H). ((E):(Z)=1:2)

MS m/e (% abundance): 320 (M$^+$, 38) 180 (25), 154 (50), 75 (15) and 73 (100).

3-(1,2-Dihydroxytridecyl)-5-trimethylsilylfuran

Pyridine (31 μl, 0.38 mmol), followed by osmium tetroxide (a 2.5% by weight solution in tert-butanol; 5 drops) was added to a solution of (E), (Z)-3-(1- tridecenyl)-5-trimethylsilylfuran (111 mg, 0.35 mmol) and N-methylmorpholine N-oxide (45 mg, 0.38 mmol) and acetone (2 ml) at room temperature. After stirring for 4 days, the mixture was acidified (dilute hydrochloric acid) and extracted thoroughly with ethyl acetate. The extracts were combined, dried (magnesium sulphate) and evaporated down to give an oil, which was flash chromatographed on silica using 60% ethyl ether/hexane,. Fractions with R$_f$ of about 0.26 and 0.21 (mixture of diasteriomers) on evaporation gave the title diol as an off-white solid.

$^1$H NMR (CDCl$_3$) (mixture of diasteriomers): 0.26 (s, 3H), 0.88 (t, 3H, J=6.5 Hz), 1.26–1.60 (m, 2H), 3.55–3.85 (m, 1H), 4.45 (d, 1H), 4.65 (d, 1H), 6.60 (s, 1H), 6.66 (s, 1H) and 7.63 (s, 1H).

MS m/e (% abundance): 354 (M$^+$, 4) 339 (2) 321 (1), 171 (17), 170 (100), 169 (87), 153 (13), 98 (16), 75 (13), 73 (59), 57 (11) and 55 (12).

3-(1,2,Diacetoxytridecyl)-5-trimethylsilylfuran

A mixture of 4-(1,2-dihydroxytridecyl)-5-trimethylsilylfuran (110 mg, 0.31 mmol), acetic anhydride (1.5 ml) and pyridine (1.5 ml) was stirred at room temperature for 13 hours. After most of the solvent was removed under high vacuum, the residue was dissolved in dichloromethane and washed thoroughly with aqueous copper sulphate. Evaporation of the dried (magnesium sulphate) organic phase gave an oil, which was purified by flash chromatography using 10% ethyl ether/hexane. Fractions with R$_f$ of about 0.52 and 0.46 (mixture of diasteriomers) on evaporation gave the title diacetate.

$^1$H NMR (CDCl$_3$) (mixture of diasteriomers): 0.29, 0.30 (2s, 9H), 0.92 (t, 3H, J=7.0 Hz), 1.30 (br, 18H), 1.50 (m, 2H), 2.09, 2.10, 2.11, 2.12 (4s), 5.25 (m, 1H), 5.88 (d, 1H, J=7.5 Hz), 5.95 (d, 1H, J=3.5 Hz), 6.63 (s, 1H), 6.65 (s, 1H), 7.66 (s, 1H) and 7.67 (s, 1H).

MS m/e (% abundance): 438 (M$^+$, 2) 423 (2), 407 (2), 391 (6), 379 (100), 337 (16), 336 (23), 169 (23), 117 (13), 73 (16) and 61 (14).

4-(1,2-Diacetoxytridecyl)-5-hydroxy-2(5H)-furanone

A mixture of 3-(1,2-diacetoxytridecyl)-5-trimethylsilylfuran (82 mg, 0.19 mmol) and Rose Bengal (5 mg) in tetrahydrofuran (7 ml) was exposed to singlet oxygen at −78° for 3 hours. The residue, after solvent removal, was purified by preparative TLC (silica developed with 60% ethyl ether/hexane). The title furanone was obtained as a pale yellow oil.

$^1$H NMR (CDCl$_3$) (mixture of diasteriomers): 0.9 (t, 3H, J=6.4 Hz), 1.27 (brs, 18H), 1.65 (br, 2H), 2.10, 2.11, 2.17, 2.21 (4s, 12H), 5.21 (brt, 1H), 5.50–5.80 (2 brm, 2H), 6.03 (brs, 1H), 6.13 (brs, 1H) and 6.16 (brs, 1H).

$^{13}$C NMR (CDCl3): 14.1, 20.6, 20.7, 20.9, 22.6, 25.2, 25.3, 29.1, 29.2, 29.3, 29.4, 29.5, 31.8, 70.0, 72.7, 98.2, 120.5, 121.2, 161.2, 164.0, 170.1 and 171.2.

MS m/e: Exact mass calculated for $C_{21}H_{38}NO_7$ $(M+NH_4)^{30}$ 416.2648, found 416.2652.

4-(1,2-Diacetoxytridecyl)-2(5H)-furanone

By the procedure of Example 5, sodium borohydride is added to the above prepared hydroxyfuranone in tetrahydrofuran and methanol at room temperature. Stirring for two hours, then working up as in Example 6 gives the title furanone compound.

EXAMPLE 11

4-[1-(2-Methoxyethoxy)methoxytridecyl]-2-trimethylsilylfuran

A mixture of 1-bromododecane (222 mg, 0.89 mmol) and magnesium turnings (22 mg, 0.94 mmol) in tetrahydrofuran (5 ml) was refluxed under argon for 1 hour. After cooling to 0°, a solution of 5-trimethylsilyl-3-furaldehyde (150 mg, 0.89 mmol) in tetrahydrofuran (1 ml) was added and conditions maintained for 1 hour. 2-Methoxyethoxymethyl chloride (0.15 ml, 1.34 mmol) was added and stirring was continued at room temperature for 16 hours. The mixture was quenched with water and extracted with ethyl ether. Evaporation of the dried (magnesium sulphate) extracts gave an oil, which was purified by preparative TLC (silica plate; developed with 15% ethyl ether/petroleum ether). The title trimethylsilylfuran was obtained as a pale yellow oil.

$^1$H NMR (CDCl3): 0.28 (s, 9H), 0.91 (t, 3H, J=6.8 Hz), 1.28 (brs, 20H), 1.75 (m, 1H), 1.85 (m, 1H), 3.43 (s, 3H), 3.55 (m, 2H), 3.65 (m, 1H), 3.85 (m, 1H), 4.61 (t, 1H, J=7.3 Hz), 4.68 (dd, 2H), 6.60 (s, 1H) and 7.58 (s, 1H).

MS m/e (% abundance): 426 (M+, 3), 322 (35), 321 (100), 249 (6), 154 (9) and 89 (16).

4-[1-(2-Methoxyethoxy)methoxytridecyl]-5-hydroxy-2(5H)-furanone

A mixture of 4-[1-(2-methoxyethoxy)methoxytridecyl]-2-trimethylsilylfuran (150 mg, 0.35 mmol) and Rose Bengal (5 mg) in tetrahydrofuran (10 ml) was exposed to singlet oxygen for 2 hours at −78°. The residue, after solvent removal, was purified by preparative TLC <silica plate; developed with 70% ethyl ether/petroleum ether). The title furanone was obtained as a pale yellow oil.

$^1$H NMR (CDCl3): 0.91 (t, 3H, J=6.4 Hz), 1.29 (s, 20H), 1.75 (brm, 2H), 3.37 (s, 3H), 3.40 (m, 2H), 3.66 (m, 2H), 3.85 (m, 1H), 4.28 (m, 1H), 4.80 (dd, 2H), 5.60 (br, 1H), 5.90 (brs, 1H) and 6.10 (brs, 1H).

$^{13}$NMR (CDCl3): 14.0, 22.6, 25.2, 28.6, 28.7, 28.8, 28.9, 29.1, 29.3, 29.4, 29.6, 31.8, 35.5, 58.7, 66.8, 71.3, 73.5, 96.1, 98.1, 98.8, 118.1 and 170.3.

MS m/e: Exact mass calculated for $C_{21}H_{42}NO_6$ $(M+NH_4)^+$ 404 3012, found 404 2997.

4-[1-(2-methoxyethoxy)methoxytridecyl]-2(5H)-furanone

Treating the above prepared hydroxyfuranone with sodium borohydride by the procedure of Example 5 gives the title furanone.

EXAMPLE 12

4-(1-O-Carboethoxytridecyl)-2-trimethylsilylfuran

A mixture of 1-bromodecane (81 mg, 0.33 mmol) and magnesium turnings (8 mg, 0.33 mmol) in THF (1.0 ml) was refluxed under nitrogen for 30 minutes. After cooling to 0°, a solution of 5-trimethylsilyl-3-furaldehyde (50 mg, 0.30 mmol) in tetrahydrofuran (0.5 ml) was added. The solution was stirred for one hour while the cooling bath warmed to room temperature. Ethylchloroformate (64 mg, 0.59 mmol) was added and the solution stirred at room temperature until no starting material remained (as monitored by TLC). The mixture was quenched with water and the organic phase was dried over magnesium sulfate, filtered and concentrated. The residue was purified by preparative TLC (silica plate; developed with 5% ethyl ether/hexane). The titled compound was obtained as a colorless oil.

$^1$H NMR (CDCl3): δ 7.64 (s, 1H), δ 6.62 (s, 1H), 5.6 (t, J=7.5 Hz, 1H), δ 4.16 (m, 2H), δ 1.9 (m, 1H), δ 1.8 (m, 1H), δ 1.26 (m, 23H), δ 0.85 (t, J=7.5 Hz, 3H), δ 0.25 (s, 9H).

4-(1-O-Carboethoxytridecyl)-5-hydroxy-2(5H)-furanone

A mixture of 4-(1-O-carboethoxytridecyl)-2-trimethylsilylfuran (43.3 mg, 0.10 mmol) and Rose Bengal (5 mg) in THF (5 ml) was exposed to singlet oxygen at −78° for four hours. The residue, after solvent removal, was purified by preparative TLC (silica plate; developed with 60% ethyl ether/hexane). The title furanone was obtained as a white solid.

$^1$H NMR (CDCl3): δ 6.25 (s, 1H), δ 6.08 (s, 1H), δ 6.02 (s, 1H), δ 5.35 (m, 2H), δ 4.2 (m, 2H), δ 1.84 (m, 2H), δ 1.35 (m, 23H), δ 0.85 (t, J=7.5, 3H).

$^{13}$C NMR (CDCl3): 170, 169.6, 166.6, 165.9, 155, 154.9, 119.4, 118.7, 97.9, 97.7, 76.5, 72.9, 72.8, 65, 64.7, 33.3, 33.1, 31.9, 29.5, 29.4, 29.3, 29.1, 24.9, 24.8, 22.6, 14.0.

MS m/e: Exact mass calculated for $C_{17}H_{28}O_3$ 280.2038 (M+), found 280.2046.

4-(1-O-Carboethoxytridecyl)-2(5H)-furanone

Treating the above prepared hydroxyfuranone with sodium borohydride by the procedure of Example 6 gives the title furanone.

EXAMPLE 13

4-Tridecyl-5-hydroxy-2(5H)-furanone

A mixture of (E), (Z)-4-(1-tridecenyl)-2-trimethylsilylfuran (2.0 g, 6.25 mmol) and 10% palladium or carbon (20 mg) in ethyl ether (10 ml) was hydrogenated at room temperature for 7 h. The mixture was filtered through celite and the filtrate upon evaporation,gave essentially pure 4-tridecyl-2-trimethylsilylfuran. The silylfuran was redissolved in tetrahydrofuran (8 ml) and was exposed to singlet oxygen, in the presence of Rose Bengal (5 mg), for 2 h at 0°. The residue, after solvent removal, was purified by a silica column using 60% ethyl ether/hexane to give the titled furanone.

$^1$H NMR (CDCl3): 0.90 (t, 3H), 1.25 (brs, 20H), 1.60 (m, 2H), 2.50 (m, 2H), 4.0 (brd, 1H), 5.85 (brs, 1H) and 6.05 (brd, 1H).

LRMS (m/e, % abundance) 283 (M+H)+, 26) 282 (M+, 37), 264 (14), 253 (11), 236 (20), 235 (11), 205 (10), 204 (12), 165 (15), 152 (19), 151 (23), 138 (34), 137 (37), 124 (25), 123 (30), 114 (26), 110 (39), 98 (58), 97 (76), 96 (61), 95 (50) and 81 (61).

6 4-Tridecyl-2(5H)-furanone

Sodium borohydride (29.5 mg, 0.78 mmol) was added portionwise to a solution of 4-tridecyl-5-hydroxy-2(5H)-furanone (218.5 mg, 0.78 mmol) in methanol (1 ml) and tetrahydrofuran (5 ml) at room temperature, After 6 h at room temperature, most of the solvent was removed and the residue was acidified with dilute hydrochloric acid. Extraction (ethyl acetate) and evaporation of the dried (magnesium sulfate) extracts gave an oil, which was purified by a silica column using 30% ethyl ether/hexane. Fractions with $R_f$ of about 0.14 on evaporation gave the titled furanone.

$^1$H NMR (CDCl$_3$): 0.88 (t, 3H, J=7.0 Hz), 1.26 (brs, 20H), 1.60 (m, 2H), 2.40 (t, 2H, J=8.0 Hz), 4.73 (brs, 2H) and 5.84 (t, 1H, J=1.6 Hz).

$^{13}$C NMR (CDCl$_3$): 13.8, 22.4, 26.9, 28.3, 28.9, 29.1, 29.2, 29.3, 29.5, 31.6, 72.9,115.3, 171.0 and 174.4.

HRMS exact mass calculated for $C_{17}H_{30}O_2(M^+)$ 266.2245, found 266.2245.

EXAMPLE 14

Reacting 4-(1-hydroxytridecyl)-2(5H)-furanone with diethyl chlorophosphate give 4-(1-diethylphosphonyl)-tridecyl-2(5H)-furanone.

EXAMPLE 15

Reacting 4-(1-diethylphosphonyl )tridecyl-2(5H)-furanone with bromotrimethylsilane gives 4-(1-phosphonyl)tridecyl-2(5H)-furanone.

EXAMPLE 16

Reacting 4-(1-hydroxytridecyl)-2-trimethylsilylfuran with diphenylphosphonyl azide and diethyl azidocarboxylate gives 4-(1-azidotridecyl)-2-triethylsilylfuran. Reducing this azide with lithium aluminum hydride gives 4-(1-aminotridecyl)-2-triethylsilylfuran. Acetylation of this intermediate with acetic anhydride gives 4-(1-acetamido)tridecyl-2-triethylsilylfuran. Oxidizing this amide with oxygen using Rose Bengal as an initiator gives 4-(1-acetamido)-5-hydroxy-2(5H)-furanone. Reduction of this furanone with sodium borohydride gives 4-(1-acetamido)-2(5H)-furanone.

EXAMPLE 17

Reacting 4-(1-aminotridecyl)-2-triethylsilylfuran with methanesulfonyl chloride gives 4-(1-methanesulfonylamido)-2-triethylsilylfuran. Oxidizing this sulfonamide with oxygen using Rose Bengal as an initiator gives 4-(1-methanesulfonylamido)-5-hydroxy-2(5H)-furanone. Reduction of this furanone gives 4-(1-methane-sulfonylamido)-5-hydroxy-2(5H)-furanone.

EXAMPLE 18

As in example 17, but substituting methanesulfonyl chloride with chlorosulfonyl isocyanate and carry through the reaction sequence gives 4-(1-uredotridecyl )-2(5H)-furanone.

EXAMPLE 19

The following test procedures may be used to demonstrate activity of the compounds of this invention:

Calcium Channel (Mobilization) Inhibition Assay

Polymorphonuclear leukocytes (PMNa), gastric glands, GH$_3$ cells, A431 cells, spleen cells, human keratinocytes corneal cells, etc. were loaded with the Ca$^{2+}$ sensitive fluorescent dye, Fura-2. The appropriate cell type was chosen and the potency and efficacy of the anti-inflammatory furanones on calcium mobilization, calcium channel inhibition quantitated. The methods used for A431 cells listed below are representative of those used for other cells.

A431 cells were detached using a 5–10 min trypsin-EDTA treatment whereas GH$_3$ cells were treated 2 to 5 min with a 1% pancreatin solution. Cells were immediately washed twice in a 20 mM HEPES buffer (pH 7.4) containing 120 mM NaCl, 6 mM KCl, 1 mM MgSO$_4$, 1 mg/ml glucose and 1 mg/ml pyruvate and 1.4 mM calcium (medium A). Approximately $5 \times 10^6$ cells were suspended in medium A and incubated with 4 µM fura-2-AM for 15 min at 37° C.

After washing the fura-2 loaded cells, the uptake of dye was checked using fluorescence micioscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. [Ca$^{2+}$]$_i$ was calculated using the following formula:

$$[CA^{2+}]_i = \frac{F - F\min}{F_{max} - F}$$

All fluorescence values were measured relative to a EGTA-quenched signal determined as follows: F was the relative fluorescence measurement of the sample. $F_{max}$ was determined by lysing the cells with digitonin (100 µg/ml) in DMSO. After $F_{max}$ was determined the pH was adjusted to 8, with NaOH and Ca$^{2+}$ chelated with 3 mM EGTA to totally quench the fura-2 signal and obtain $F_{min}$.

When quin-2 was used, cells were Incubated with 10 µM quin-2 at 37° C. for 1 hr, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., Clin Pharmacol Ther (1974) 16:900–904].

Compounds of this invention demonstrate weak or no activity In the following test procedures:

Inhibition of Phospholipase A$_2$

The effect of compounds of this invention on bee venom phospholipase A$_2$ Is determined by the following procedure:

a. Bee venom phospholipase A$_2$ in 10 µM HEPES (pH 7.4) with 1 mM CaCl$_2$ is incubated with vehicle or test agent for 1.0 hour at 41°.

b. 1.36 mM phosphotidylcholine, 2.76 mM Triton X-100 are dispersed in buffer by sonication and then mixed with L-3 phosphotidylcholine, 1-palmitoyl-2-1-$^{14}$C) palmitoyl for 10 min.

c. Start the reaction by the addition of enzyme (0.495 units/ml).

d. Incubation for 15 sec. at 41°.

e. Reaction is terminated by addition of 2.5 ml of isopropanol: n-heptane: 0.5M H$_2$SO$_4$ (40:10:1; v:v:v).

f. 2.0 ml n-heptane and 1.0 ml H$_2$O added; mixture centrifuged.

g. 2.0 ml n-heptane removed and treated with 200–300 mg of silica gel HR60.

h. Samples centrifuged; 1 ml of n-heptane SN removed and added to 10 ml scintillation fluid.

i. Samples counted on a scintillation counter.

Inhibition of Phosphoinositide-specific Phospholipase C

The effect of compounds of this invention on phosphoinositide-specific phospholipase-C may be determined by procedures described by Bennett et al, *Molecular Pharmacology* 32:587–593 (1987).

What is claimed is:

1. A process for administering to a mammal for therapeutic purposes an effective amount of a calcium channel inhibitory compound of the formula

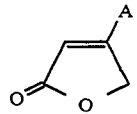

where A is C$_{10}$–C$_{20}$alkyl.

2. The process of claim 1 where the compound is 4-tridecyl-2(5H)-furanone.

3. The process of claim 1 where the calcium channel inhibitory compound is administered in a daily dose of approximately 0.05 to 100 mg per kilogram body weight of the mammal.

* * * * *

UNITED STATES PATENT AND TRADEMARK OFFICE
CERTIFICATE OF CORRECTION

PATENT NO. : 5,376,676
DATED : December 27, 1994
INVENTOR(S) : Gary C.M. Lee

It is certified that error appears in the above-identified patent and that said Letters Patent is hereby corrected as shown below:

Column 1, in both formulas of seco-manoalide and dehyfro-seco-manoalide "OHO" should be --CHO--;

Column 4, line 40, "Is" should be --is--;

Column 7, line 35, "13_c" should be --$^{13}C$--;

Column 10, line 21, "7:61" shouod be --7.61--;

Column 10, line 33, "0,9 mmol" should be --0.9 mmol--;

Column 10, line 47, "29i3" should be --29.3--;

Column 14, line 33, after "339(2)" please insert --,--;

Column 14, line 38, "3-(1,2," shoud be --3-(1,2- --;

Column 14, line 55, berfore "423" please insert --,--;

column 15, line 3, "(CDC13)" should be --($CDCl_3$)--;

Column 15, ine 7, "$(M+NH_4)^{30}$" should be --$(M+NH_4)^+$--;

Column 15, line 50, "〈silica" should be --(silica--;

Column 17, line 4, "6 4-Tridecyl" should be --4-Tridecyl---;

Column 17, line 8, "temperature," should be --temperature.--;

UNITED STATES PATENT AND TRADEMARK OFFICE
CERTIFICATE OF CORRECTION

PATENT NO. : 5,376,676

DATED : December 27, 1994

INVENTOR(S) : Gary C.M. Lee

It is certified that error appears in the above-identified patent and that said Letters Patent is hereby corrected as shown below:

Column 18, line 54, "In" should be --in--;

Column 18, line 57, "Is" should be --is--.

Signed and Sealed this

Second Day of May, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,376,676
DATED : December 27, 1994
INVENTOR(S) : Gary C.M. Lee

It is certified that error appears in the above-identified patent and that said Letters Patent is hereby corrected as shown below:

Column 5, line 2, "selctive" shoud be --selective--;

Column 9, line 20, "(M+)" should be --($M^+$)--;

Column 16, lines 20 and 34, " 'H" should be --$^1H$--;

Column 16, line 66, "$(M+H)^+$, 26)" should be --($(M+H)^+$, 26),--.

Signed and Sealed this

Eleventh Day of July, 1995

Attest:

BRUCE LEHMAN

*Attesting Officer*  *Commissioner of Patents and Trademarks*